(12) United States Patent
Cohen et al.

(10) Patent No.: US 10,706,261 B2
(45) Date of Patent: Jul. 7, 2020

(54) SYSTEM AND METHOD FOR AUTOMATICALLY ANALYZING PHENOTYPICAL RESPONSES OF CELLS

(71) Applicant: Molecular Devices, LLC, San Jose, CA (US)

(72) Inventors: Avrum Isaac Cohen, Downingtown, PA (US); Dihui Hong, Chester Springs, PA (US)

(73) Assignee: Molecular Devices, LLC, San Jose, CA (US)

( * ) Notice: Subject to any disclaimer, the term of this patent is extended or adjusted under 35 U.S.C. 154(b) by 200 days.

(21) Appl. No.: 15/750,579

(22) PCT Filed: Aug. 5, 2016

(86) PCT No.: PCT/US2016/045784
§ 371 (c)(1),
(2) Date: Feb. 6, 2018

(87) PCT Pub. No.: WO2017/027380
PCT Pub. Date: Feb. 16, 2017

(65) Prior Publication Data
US 2019/0012521 A1    Jan. 10, 2019

Related U.S. Application Data

(60) Provisional application No. 62/204,225, filed on Aug. 12, 2015.

(51) Int. Cl.
*G06K 9/00* (2006.01)
*G16B 40/00* (2019.01)
(Continued)

(52) U.S. Cl.
CPC ..... *G06K 9/00147* (2013.01); *G01N 33/5008* (2013.01); *G06T 7/0012* (2013.01);
(Continued)

(58) Field of Classification Search
CPC ......... G06T 7/0012–0016; G06T 2207/20081; G06T 2207/20084; G06T 2207/30024;
(Continued)

(56) References Cited

U.S. PATENT DOCUMENTS

| 2005/0137806 A1* | 6/2005 | Kutsyy | .............. | G06K 9/00147 |
| | | | | 702/19 |
| 2007/0208516 A1* | 9/2007 | Kutsyy | .............. | G06K 9/00147 |
| | | | | 702/19 |

(Continued)

FOREIGN PATENT DOCUMENTS

JP    2013188193 A    9/2013

OTHER PUBLICATIONS

International Search Report and Written Opinion for PCT/US2016/045784 dated Dec. 2, 2016.

*Primary Examiner* — Justin P. Misleh
(74) *Attorney, Agent, or Firm* — McCracken & Gillen LLC (57) ABSTRACT

A system and a method to analyze a phenotypical response of cells to a treatment are disclosed in which a model development module receives images of a plurality of reference cell carriers and treatment information associated with the plurality of reference cell carriers, identifies parameters of cells in the image that distinguish those reference cell carriers to which the treatment has been applied from other reference cell carriers, and trains a model using the identified parameters. A high-content imaging system includes an image capture device, and the image acquisition module receives from the image capture device a plurality of images of cell carriers to be evaluated. The model application module applies the trained model to the plurality of (Continued)

images of the cell carriers to be evaluated to predict a concentration of the treatment applied to each of the cell carriers evaluated.

20 Claims, 5 Drawing Sheets

(51) Int. Cl.
    *G06T 7/00*     (2017.01)
    *G01N 33/50*     (2006.01)

(52) U.S. Cl.
    CPC .... *G16B 40/00* (2019.02); *G06T 2207/20081* (2013.01); *G06T 2207/20084* (2013.01); *G06T 2207/30024* (2013.01); *G06T 2207/30072* (2013.01)

(58) Field of Classification Search
    CPC ..... G06T 2207/30072; G06K 9/00127–00147; G16B 40/00; G01N 33/5008–5094
    See application file for complete search history.

(56) References Cited

U.S. PATENT DOCUMENTS

| | | | |
|---|---|---|---|
| 2007/0250270 A1* | 10/2007 | Vaisberg | C12Q 1/6827 |
| | | | 702/19 |
| 2007/0250301 A1* | 10/2007 | Vaisberg | G01N 15/1475 |
| | | | 703/11 |
| 2009/0024331 A1 | 1/2009 | Tomaney et al. | |
| 2009/0169089 A1 | 7/2009 | Hunt et al. | |
| 2013/0121557 A1* | 5/2013 | Alexandrov | G06T 7/0014 |
| | | | 382/133 |
| 2013/0274838 A1 | 10/2013 | Entcheva et al. | |
| 2015/0087240 A1 | 3/2015 | Loewke et al. | |

* cited by examiner

|   | 1 | 2 | 3 | 4 | 5 | 6 | 7 | 8 | 9 | 10 | 11 | 12 |
|---|---|---|---|---|---|---|---|---|---|----|----|----|
| A | + | + | + | + | + | + | − | − | − | − | − | − |
| B | + | + | + | + | + | + | − | − | − | − | − | − |
| C | + | + | + | + | + | + | − | − | − | − | − | − |
| D | + | + | + | + | + | + | − | − | − | − | − | − |
| E | + | + | + | + | + | + | − | − | − | − | − | − |
| F | + | + | + | + | + | + | − | − | − | − | − | − |

FIG. 4

|   | 1 | 2 | 3 | 4 | 5 | 6 | 7 | 8 | 9 | 10 | 11 | 12 |
|---|---|---|---|---|---|---|---|---|---|----|----|----|
| A | − | − | − | 1 | 1 | 1 | 2 | 2 | 2 | 3 | 3 | 3 |
| B | − | − | − | 1 | 1 | 1 | 2 | 2 | 2 | 3 | 3 | 3 |
| C | − | − | − | 1 | 1 | 1 | 2 | 2 | 2 | 3 | 3 | 3 |
| D | 4 | 4 | 4 | 5 | 5 | 5 | 6 | 6 | 6 | 7 | 7 | 7 |
| E | 4 | 4 | 4 | 5 | 5 | 5 | 6 | 6 | 6 | 7 | 7 | 7 |
| F | 4 | 4 | 4 | 5 | 5 | 5 | 6 | 6 | 6 | 7 | 7 | 7 |

FIG. 5

SYSTEM AND METHOD FOR AUTOMATICALLY ANALYZING PHENOTYPICAL RESPONSES OF CELLS

RELATED APPLICATION

This application claims the benefit of U.S. Patent Application Ser. No. 62/204,225 filed Aug. 12, 2015, the content of which is incorporated by reference herein in its entirety.

FIELD OF DISCLOSURE

The present subject matter relates to high content imaging systems, and more particularly, to a system and method to automatically analyze phenotypical responses of cells.

BACKGROUND

A researcher may use a high content imaging system (HCIS) to analyze phenotypical responses of biological cells to a treatment, such as, for example, exposure to particular substances and/or other environmental changes. Such responses may be visually distinct and may be observable in images acquired using fluorescent labeling and other techniques.

However, such responses may vary in accordance with the pathway involved in the response, cell tissue type, cell age, growing condition, and the like. The variety of possible responses requires the analysis of the images of cells be limited to a particular type of phenotypical response such as, for example, translocation of a protein from one location in a cell to another, expression or presence of a particular molecule, congregation or clumping of a molecule, and the like. Further, each type of phenotypical response that may be analyzed may be associated with a plurality of adjustable parameters that may be measured in images of such cells, and the presence or absence of such response may be indicated by a magnitude of such measured parameters. The quantity of the types of responses and the number of parameters that must be adjusted to quantify each type of response may pose a significant burden on a researcher because the researcher must identify the phenotypic type of response that occurs, and then manipulate the various parameters associated with such type to determine if such response did indeed occur.

Further, in some cases, it may not be practical or even possible to expose a homogenous population of target cells to a substance or environmental condition to be tested. In such cases, a heterogeneous population of cells that includes the target cells are exposed to the substance or environmental condition, images of the heterogeneous population are acquired, and such images have to be analyzed to determine if the particular target cell in the heterogeneous population exhibits a particular phenotypical response.

SUMMARY

According to one aspect, a system to analyze a phenotypical response of cells to a treatment includes a high-content imaging system and a response analysis system that includes computer-executable code stored on one or more non-transitory storage devices that, when executed, causes one or more processors to receive images of a plurality of reference cell carriers and treatment information associated with the plurality of reference cell carriers, identify parameters of cells in the plurality of reference cell carriers from the images based on the treatment information, the parameters distinguishing those cells in the reference cell carriers to which the treatment has been applied from other cells in the plurality of reference cell carriers, and train a model using the identified parameters. The high-content imaging system includes an image capture device, and the executable code further causes the one or more processors to receive from the image capture device a plurality of images of cell carriers to be evaluated and apply the trained model to the plurality of images of the cell carriers to be evaluated to indicate a response level of cells in each of the cell carriers evaluated.

According to another aspect, a method for analyzing a phenotypical response of cells to a treatment includes operating a high-content imaging system, wherein the high-content imaging system includes an image capture device. The method also includes receiving images of a plurality of reference cell carriers and treatment information associated with the plurality of reference cell carriers, identifying parameters of cells in the plurality of reference cell carriers from the images, the parameters distinguishing those cells in the plurality of reference cell carriers to which the treatment has been applied from other cells in the plurality of reference cell carriers, and training a model using the identified parameters. The method further includes operating the image capture device of the high-content imaging system to obtain a plurality of images of cell carriers to be evaluated, and applying the trained model to the plurality of images of the cell carriers to be evaluated to predict a concentration of the treatment applied to each cell carrier of the plurality of the cell carriers to be evaluated.

Other aspects and advantages will become apparent upon consideration of the following detailed description and the attached drawings wherein like numerals designate like structures throughout the specification.

DETAILED DESCRIPTION

Figure 1:
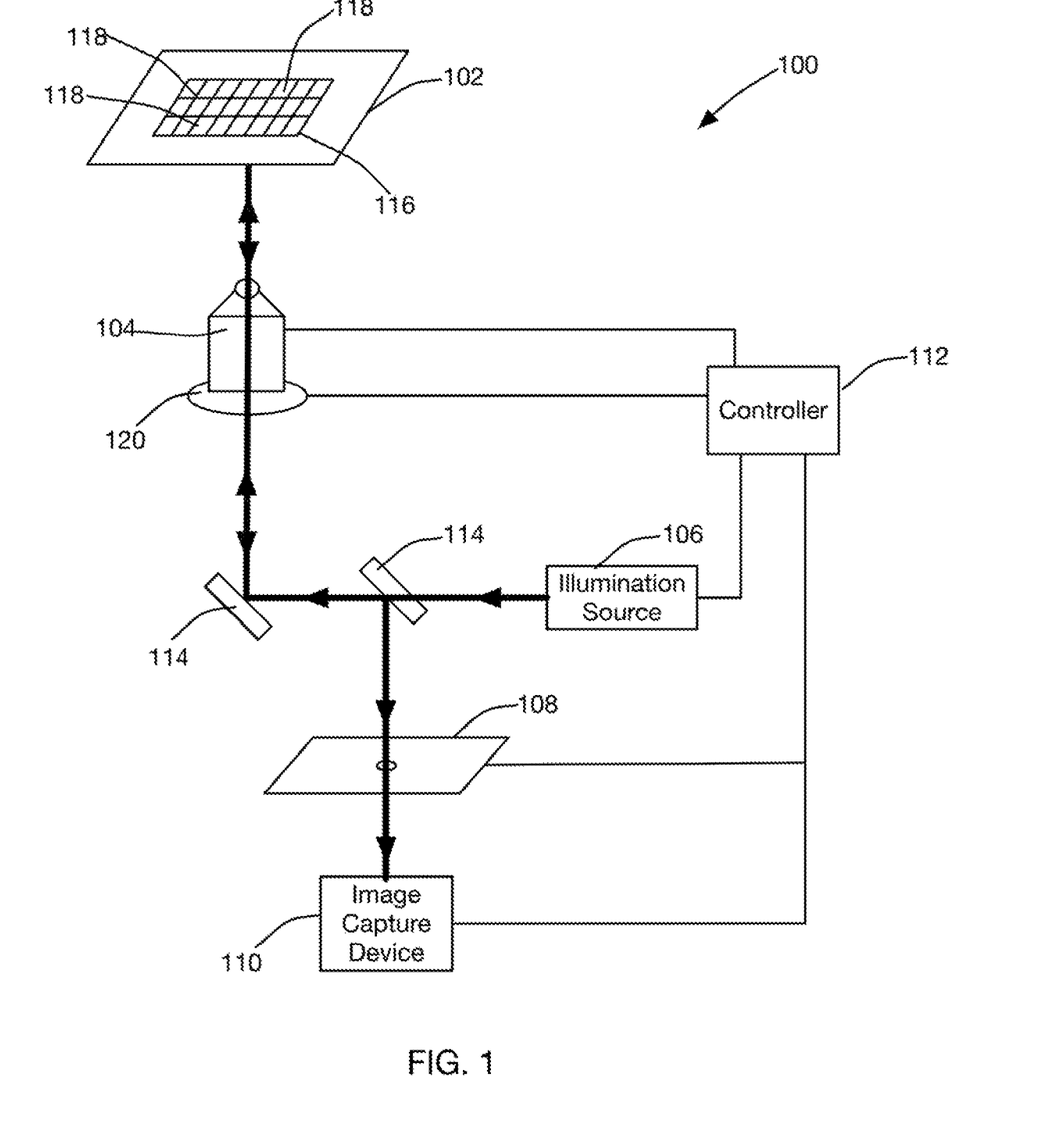
FIG. 1 is a block diagram of a high content imaging system.

Referring to FIG. 1, as will be apparent to those who have skill in the art, an HCIS 100 may include an X-Y stage 102, one or more objective lenses 104, one or more illumination sources 106, one or more filters 108, an image capture device 110, and a controller 112. The HCIS 100 may also include one or more mirrors 114 that direct light from the illumination source 106 to a sample tray 116 that may be disposed on the X-Y stage 102, and from such sample tray 116 to the image capture device 110. Typically, the sample tray 116 includes a plurality of wells 118, and samples (for example, biological cells) to be imaged by the HCIS 100 may be disposed in each such well 118.

Although, FIG. 1 shows the light from the illumination source 106 reflected from sample tray 116 reaching the image capture device 110, it should be apparent that additional mirrors (not shown) may be used so that light from the illumination source 106 is transmitted through the sample tray 116 and directed toward the image capture device 110. Further, it should be apparent that in some cases no illumination from the illumination source 106 may be necessary to image the samples in the sample tray 116 (for example, if the samples emit light or if the samples include radioactive components). In some embodiments, light from the illumination source may be transmitted through the samples in the sample tray 116, and the samples refract and/or absorb the transmitted light to product lit that is imaged.

During operation, the sample tray 116 may be placed, either manually or robotically, on the X-Y stage 102. In addition, the controller 112 may configure the HCIS 100 to use a combination of a particular objective lens 104, illumination generated by the illumination source 106, and/or filter 108. For example, the controller 112 may operate positioning devices (not shown) to place a selected objective lens 104 and, optionally, a selected filter 108 in the light path between the sample tray 116 and the image capture device 110. The controller 112 may also direct the illumination source 106 to illuminate the sample tray 116 with particular wavelengths of light. The samples in the sample tray 116 may contain molecules that fluoresce, either naturally occurring molecules, or molecules produced or present within the samples due to treatment. The wavelength illuminating the sample may be the excitation wavelengths associated with such fluorescent molecules, and the imaging capture device will capture only the emission spectrum of such fluorescent materials. One or more wavelengths may used serially or simultaneously to illuminate the same samples and produce images In addition, in some embodiments, the controller 112 may operate a focus mechanism 120 so that the image capture device 110 may obtain in-focus images of samples disposed in the sample tray 116.

Thereafter, the controller 112 may operate the X-Y stage 102 so that a well 118 or a portion thereof is in a field of view of the image capture device 110, and actuate the image capture device 110 to capture an image of the well 118 or the portion thereof. The controller 112 may repeatedly operate the X-Y stage 102 and the image capture device 110 in this manner until images have been captured of all of the wells 118 of the sample tray 116 that are of interest. Further, the controller 112 may capture several images of the same well 118 or portion thereof, wherein each such image is captured using a different combination of one of the objective lenses 104, one or more of the filters 108, and illumination generated by the illumination source 106.

Referring to FIGS. 1-4, a response analysis system 200 may be used with the HCIS 100 to automatically determine if any cells disposed in the wells 118 of the sample tray 116 are responsive to a treatment. A reference sample tray 116A is prepared with identical populations of sample cells disposed in each well 118A thereof. The population disposed in each well 118A may be a homogeneous population that comprises only target cells, or a heterogeneous population that is a combination of target cells and non-target cells. Thereafter, selected wells 118A of the reference sample tray 116A may be subjected to a treatment.

Figure 3:
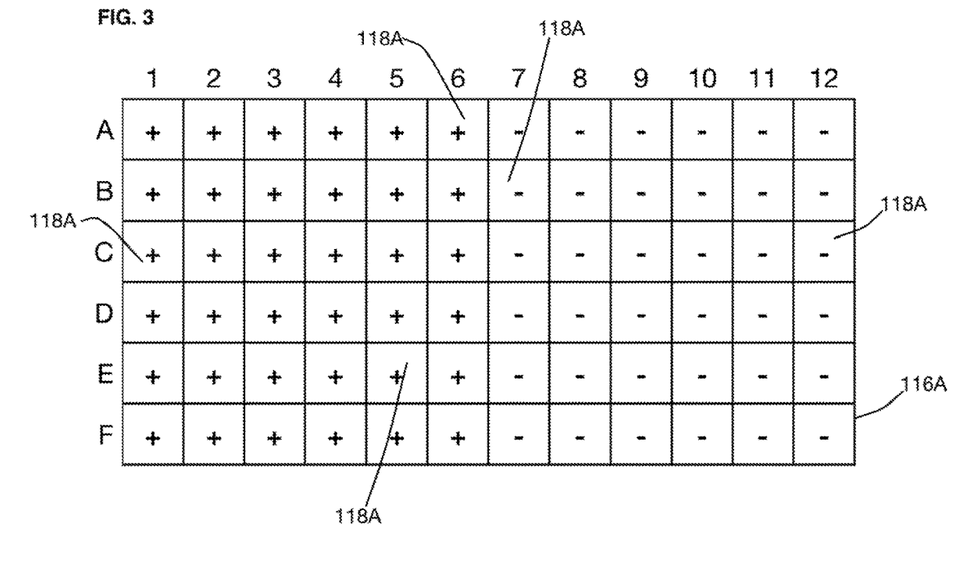
FIGS. 3 and 4 illustrate sample trays that may be used with the response analysis system of FIG. 2.

In some embodiments, selected wells 118A of the reference sample tray 116A may either have a predetermined dose or concentration of the treatment applied thereto, and other wells 118A may have no treatment applied thereto. As illustrated in FIG. 3, the wells 118A in columns 1-6 may have been subjected to the treatment, as indicated by the "+" character, and the wells 118A in columns 7-12 may not have been subjected to the treatment, as indicated by the "−" character.

Figure 4:
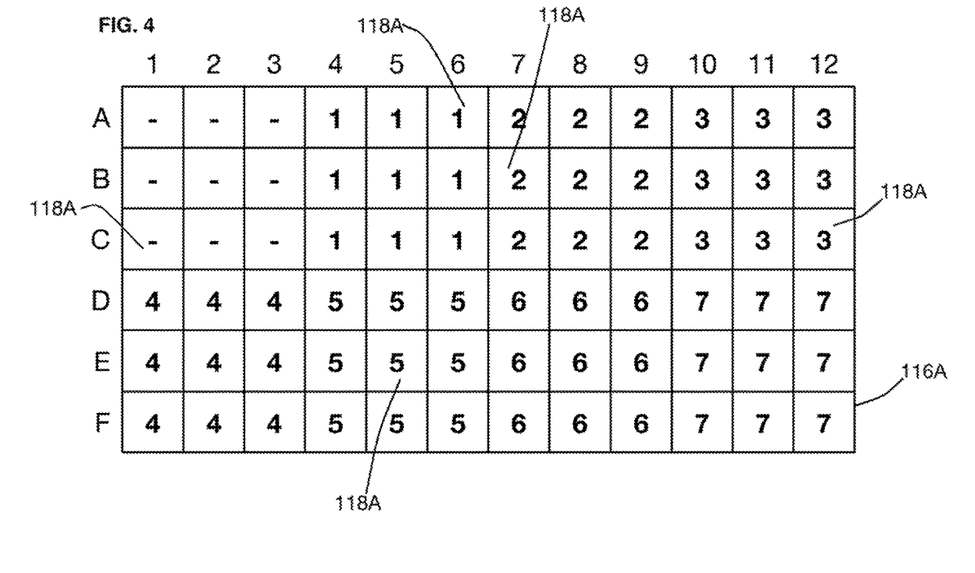

In some embodiments, the wells 118A of the reference sample tray 116A may have different dosages or concentrations of the treatment applied thereto. As illustrated in FIG. 4, the wells 118A in rows A-C and columns 1-3 have not had any treatment applied thereto, as indicated by the "−" character. The wells 118A in rows A-C and columns 4-6 have had a first concentration, for example, one unit of the treatment applied thereto as indicated by the "1" character, the wells 118B in rows A-C and columns 7-9 have had a second concentration, for example, two units of the treatment applied thereto as indicated by the "2" character. In the present example shown in FIGS. 3 and 4, each unique character shown in the wells 118A of the reference sample tray 116A is associated with a different concentration of the treatment applied to such wells.

Figure 2:
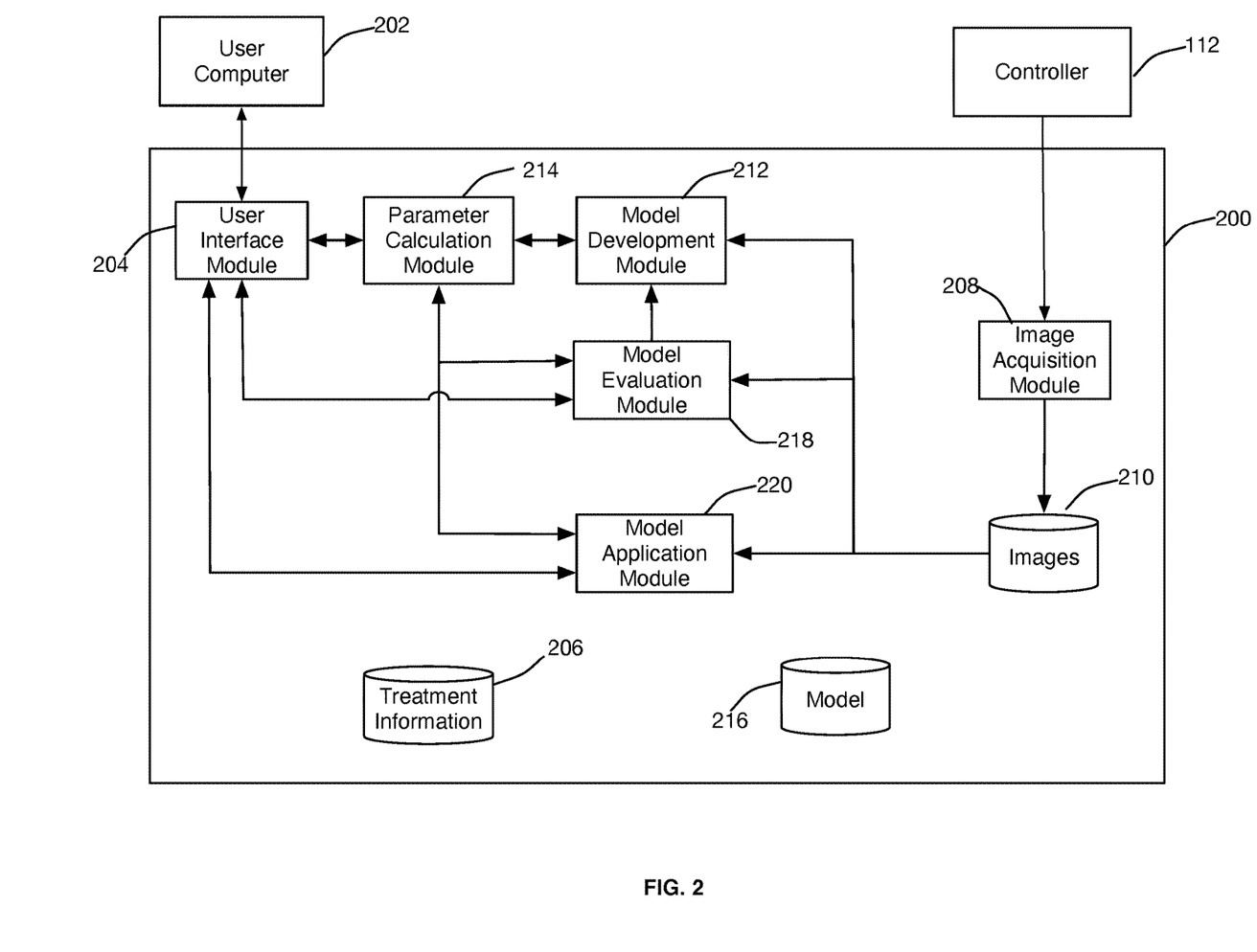
FIG. 2 is a block diagram of a response analysis system that may be used with the high content imaging system of FIG. 1.

An operator uses the user computer 202 to specify treatment information to the response analysis system 200, and such treatment information includes an indication of the concentration of the treatment applied to each well 118A of the reference sample tray 116A. A user interface module 204 receives such reference sample tray information and stores the information in a treatment information database 206. In some embodiments the user interface module 204 allows the operator to upload a file, for example, a text file, a spreadsheet file, or other data file that specifies, for each well 118A of the reference sample tray 116A, a concentration or amount of the treatment applied to such well 118A. In other embodiments, the user interface module 204 displays on the user computer 202 a representation of the wells 118A of the reference sample tray 116A, and allows the operator to use an input device (not shown) of the user computer 202 to select a representation of each well, and indicate a concentration of the treatment applied to each well 118A associated with such representation. Other ways apparent to those who have skill in the art may be used to supply the reference sample tray information to the response analysis system 200.

Thereafter, an image acquisition module 208 directs the HCIS 100 to capture a plurality of images of each well 118A, wherein each image is captured with a different combination of the objective lens 104, illumination generated by the illumination source 106, and the filter 108, as described above. In some embodiments, such plurality of images may be acquired using different modalities, including transmitted light, flourescence, differential interference contrast, phase contrast, brightfield imaging, and the like.

In some embodiments, the image acquisition module 208 transmits each particular combination to the controller 112 of the HCIS 100, and in response receives a captured image from the image capture device 110. The received image is then stored in an images database 210. In other embodiments, the image acquisition module 208 may be integrated with the controller 112 of the HCIS 100, and automatically configures the HCIS 100 with each combination, directs the image capture device 110 to capture an image, and stores the image in the images database 210. In some embodiments, the combinations of objective lens, illumination, and filter used to capture images are predefined. In other embodiments, the user may select such combinations in accordance with characteristics of the samples in the sample tray 116A. Such characteristics may include molecules in such samples, the size of the structures of interest in the samples, and the like.

After all of the images have been captured and stored in the images database 210, a model development module 212 analyzes the stored images of the reference sample tray 116A to develop a model. Thereafter the developed model may be used to automatically analyze images of other sample trays 116 to determine if the cells in such trays exhibit a phenotypical response to the treatment.

To develop the model, the model development module 212 may use the treatment information and randomly select a training subset of the wells 118A of the reference sample tray 116A. The training subset may include one or more wells 118A to which no treatment has been applied, and at least one well 118A for each of the different concentrations of the treatment that is applied to the sample tray 116A. For example, if the reference sample tray 116A illustrated in FIG. 4 is used, the training subset may include at least one well 118A to which no treatment has been applied, and at least one well 118A associated with each of the different concentrations 1-7 of the treatment applied to the wells 118A of the reference sample tray 116A.

The model development module 212 may provide one or more images of each well 118A to a parameter calculation module 214 for analysis. The parameter calculation module 214 analyzes the images and calculates values of various characteristics or parameters of such images. For example, the image may be analyzed to determine an average pixel intensity value thereof, values of pixel coordinates of such image where cell nuclei are located, a value that represents the strength of pixel intensity variation at edges of cells in the image, a value that represents an orientation of edges relative to nuclei of cells in the image, a value that represents a measure of texture or variation of pixel intensities at different magnifications, and the like. Further, the measure of texture may include calculating a standard deviation of pixel intensity, identifying frequencies associated with peaks of a Fourier transform of the image, wavelet matches, and Laplacian of Gaussian peak analysis.

In some embodiments, the parameter calculation module 214 may segment the images to identify cell structures associated with each cell nuclei in such images. For example, cell boundaries associated with a cell nuclei may be identified, using one or more images taken with different wavelengths of light. The area of each cell bounded by such boundaries may be calculated. Also, the model development module 212 may evaluate a shape of such cells (e.g., circular, elongated, polygonal, etc.). Further, the identified boundary of a cell may be used to mask the image to isolate structures that are associated with the cell, and values of parameters described above also may be calculated on such masked image.

In some embodiments, the parameter calculation module 214 may direct the user interface module 204 to display an image or a portion thereof on the user computer 202, and to obtain from the operator identification of pixels of the image (or portion thereof) that are associated with a cell and/or cell nuclei. Such operator provided information may be used to automatically identify boundaries associated with such cell nuclei and/or identify additional cell nuclei. It should be apparent that the parameter calculation module 214 may use filtering, machine learning, and image analysis techniques known to those of ordinary skill in the art to calculate the values the various parameters associated with the images of the wells 118A of the reference sample tray 116A.

In some embodiments, the parameter calculation module 214 may calculate values of parameters of all of the samples or cells in each well 118A or the reference sample tray 116A. Because the number of wells 118A compared to the number of samples is relatively low and the number of measurable parameters is relatively large, calculating parameters for the samples within the whole well 118A may facilitate developing inferences of how a treatment applied to the well 118A is manifested in the parameters calculated for such well 118A.

In some embodiments, the parameter calculation module 214 calculates values of the parameters that represent a measure of individual cells identified in the image of the well 118A such as, for example, a distance from a cell edge to a cell nucleus, cell shape, intensity variation within the cell, and the like. Further, the parameter calculation module 214 may use information from several images of a sample area of a particular well 118A, for example, taken using different illumination to facilitate calculations of the values of the parameters associated with a particular image of the well 118A.

Cells within the image could be identified various ways. In one embodiment, the parameter calculation module 214 identifies stained nuclei in each image. Such identification may use a machine-learning algorithm known to those of ordinary skill in the art such as used by MiniMax, or an intensity and size based algorithm. MiniMax may also be used to identify label free cells using transmitted light. To determine characteristics of parameters associated with the well 118A, exact identification of each cell in such well may not be required. However, if individual cells are identified by the parameter calculation module 214, the parameter calculation module 214 may be able to develop characteristics of parameters associated with individual cells in the well 118A in addition to characteristics parameters associated with the well 118A.

In some embodiments, sections of the image of the well 118A may be split into sections and "cell like" areas in each such sections could be identified either by features such as texture or by machine learning algorithms, as described above.

After values of the parameters have been developed from the images of the wells 118A in the subset selected by the model development module 212, the model development module 212 statistically correlates the values of the parameters associated for each well 118A with the treatment concentration actually applied to such well 118A. As noted above, information regarding the treatment concentration actually applied to the well 118A is available from the treatment information database 206.

For example, if the reference sample tray 116A includes 100 wells that have a positive treatment and 100 wells that have a negative treatment, and the 80 of the positively treated wells are associated with images that have a relatively high average image intensity and only 20 of the negatively treated wells are associated with images that have a relatively high intensity, then average image intensity may be considered a parameter that is correlated with treatment, and a high value of such parameter may be considered correlated with positive treatment.

In some embodiments, a statistical correlation coefficient, for example, a Pearsons correlation or a Spearman correlation, may be calculated between the value of each parameter associated with the well 118A and/or cell disposed in such well 118A, and the treatment concentration applied to the well 118A. In other embodiments, the number of correct predictions of the treatment concentrations associated with each parameter may be determined. Other ways to determine a correlation between the parameter of images associated with the well 118A and the treatment applied to such well 118A apparent to those of ordinary skill in the art may be used. Further, such correlations may be developed for one or more cells identified in such image.

After the parameters have been correlated, the model development module 212 selects those parameters that have the highest correlation with or best predict the treatment concentration applied to the training subset of wells 118A.

The model development module 212 may use the values of the selected parameters and machine-learning techniques to train a model that may be used to identify and/or quantify a response to treatment by cells in wells 118 of a production sample tray 116.

In one embodiment, the model development module 212 may train an artificial neural network in which each input node is associated with one of the selected parameters. The value of each parameter calculated from images of a well 118A of the training subset is provided at the input node associated with such parameter. The values at the input node are propagated through the artificial neural network to produce a value at the output node of the artificial neural network that predicts the concentration of treatment applied to such well 118A. The error between the predicted concentration of the treatment and the concentration of the treatment actually applied is calculated, and the weights of the interior nodes of the neural network are adjusted in accordance with such error, for example, using backward propagation of the error. The artificial neural network may be iterated using values at the input nodes of the parameters calculated from images of additional wells 118A of the training subset until the weights of the artificial neural network converge, and the error between predicted treatment concentrations of the wells 118A of the training subset and actual treatment concentrations applied to such wells 118A is minimized.

In other embodiments, a multiple layered neural network may be developed and deep learning methods may be used to train such network. For example, values associated with values of complex sets of parameters of the images of wells (or cells) may be provided to an input node of such a network to improve the initial variable weighting of the network. In some embodiments, a forest tree or random tree forest technique may be used in which the values of the parameters associated with each well 118A or cell disposed in the well 118A are analyzed to determine a set of parameters that generates a positive indication of treatment for those wells 118A of the training subset, or cells disposed in such wells 118A, that have had treatment applied thereto.

Metaheuristic techniques may be used to develop the model in which, for example, a genetic algorithm in which genes are associated with parameters, and the values for such parameters are coded in strands of such genes. Such strands of genes may be used to predict the treatment applied to the wells 118A of the training subset, and/or cells disposed in such wells 118A. The fraction of strands that best separate the positively treated wells 118A and/or cells from the negatively treated wells 118A and/or cells may be "mated" by interchanging genes between pairs of such strands. Over multiple iterations of such mating, lower scoring strands may be removed so that only the fittest strands survive. The trained model may comprise one such fittest (or highest scoring) strand that survives.

In still other embodiments, the model may be implemented using other machine learning techniques apparent to those who have skill in the art including decisions trees, support vector machines, k-means clustering, swarm, ant colony optimization, and simulated annealing. In some embodiments, as will be apparent to those of ordinary skill in the art, gradient descent and similar techniques may be used to speed convergence of the machine learning techniques described herein.

The parameters that comprise the inputs of the model developed by the model development module 212 are stored in a model database 216.

Thereafter, a model evaluation module 218 selects wells 118A that comprise an evaluation subset from those wells 118A of the reference sample plate 116A not in the training subset. Like the training subset, the wells 118A that make up the evaluation subset have at least one well 118A associated with each concentration of the treatment applied to the reference sample tray 116A. For each well 118A in the evaluation subset, the model evaluation module 218 provides the images from the images database 210 to the parameter calculation module 214. The parameter calculation module 214 analyzes such images to calculate values of the parameters identified by the model development module 212 as being correlated with concentration of treatment. The model evaluation module 218 then uses the calculated values as an input to the model stored in the model database 216, and calculates an error between the output of such model with the actual treatment applied to the well 118A. The model evaluation module 218 calculates such error value for each well 118A that comprises the evaluation subset. The error values are combined to develop a confidence score for the model stored in the model database 216.

In one embodiment, the error values for each well 118A may be statistically analyzed to evaluate how well the model predicts if any treatment has been applied to each well 118A or an amount of the treatment applied to each well 118A of the evaluation subset. If different amounts of treatment are applied to each well 118A of the evaluation subset, the evaluation module 218 may analyze the error bars associated with a relationship (e.g., a curve) between the amount of treatment actually applied and the amount of treatment predicted by the model.

In some embodiments, the evaluation module 218 may compare the amount of response exhibited by cells from previous experiments to the amount of response to treatment identified by the developed model. For example, suppose the treatment includes adding a toxic substance to the wells 118, and a dilution series may run among the wells 118. All of the cells in wells 118 exposed to a high concentration of the toxic substance may be killed, whereas cells in wells 118 exposed to a low concentration of the toxic substance may not show any perceptible change. Experimental data that includes images of cells exposed to different concentrations of toxin, the concentration of toxin associated with each image, and the percent of cells killed by such concentration may be provided to the evaluation module 218. The evaluation module 218 may compare the predictions of the model to such experimental data to develop error bars or confidence scores that indicate how well the model predicts the actual experimental data.

Continuing with the above example, experimental data that may be provided may also include information regarding how many cells in an image of cells exposed to a particular concentration of the toxin were actually dead and how many cells appeared dead but were actually alive (i.e., false positives). In some embodiments, the evaluation module 118 may use such additional data to develop confidence scores that indicate the ability of the model to predict or take into account false negatives or false positives. In some embodiments, the evaluation module 118 may consider situations in which all or most cells of a sample produce a continuous range of responses. For example, if a drug is known to cause cells to produce a particular protein, and at doses a minimal amount of protein may be produced and that as the dosage is increased, the amount of protein produced also increases. In such situations, the model development module 212 may train the model based on the amount of response (i.e., amount of protein produced) exhibited by cells rather than the number of cells that exhibited the response. In some embodiments, cells may have the DNA thereof modified to add a fluorescent marker (e.g., Green Fluorescent Protein) to the protein developed by the cells in response to the drug. In these cases, the expression of the protein may be measured as the protein moves outside the nucleus of the cell, and/or groups or combines with other proteins.

In some embodiments, a high value for the confidence score indicates better model performance, i.e., fewer errors between output of the model and the actual treatment applied to the wells 118A that comprise the evaluation subset. In other embodiments, a low confidence score may be associated with better model performance, wherein a confidence score of zero indicates perfect prediction of the treatment applied to the wells 118A of the evaluation subset.

In some embodiments, if a high value of the confidence score indicates better model performance and the confidence score exceeds a predetermined threshold value, the model is considered acceptable and the model may be used to analyze production sample trays 116. Similarly if a low value of the confidence score indicates better performance and the confidence score is less than a predetermined threshold value, the model is a considered acceptable.

In other embodiments, the model evaluation module 218 provides the confidence score to the user interface module 204 for display on the user computer 202. In such embodiments, the operator may indicate whether the model associated with the confidence score is acceptable or not acceptable.

If the model is not acceptable, the model development module 212 may tune the model by replacing one or more parameters used to develop the model with other parameters that show a high correlation between the parameter and the wells 118A of the training subset. Machine learning techniques as described above may be used thereafter to develop a tuned model. The tuned model may be evaluated and/or tuned further until a model is developed that produces an acceptable confidence score when applied to the evaluation subset of the wells 118A.

After the model is developed, the model may be stored in the model database 216 until needed to analyze a production sample tray 116. The model may be used with a production sample tray 116 with wells 118 in which cells similar to those used to develop model have been deposited and treated with the treatment associated with the model.

In some embodiments, when the production sample tray 116 is disposed in the HCIS 100, the user interface module 204 may display on the user computer 202 a list of models stored in the model database 216. Thereafter, the user interface module 204 may receive from the user computer 202 a selected of one of the models stored in the model database 216. The user interface module 204 provides the selected model to a model application module 220. The model application module 220 determines the parameters required to apply the model, and the image capture parameters necessary to obtain values of such parameters. The model application module 220 directs the image acquisition module 208 to obtain the necessary images of each well 118 of the production sample tray 116, and uses the parameter calculation module 214 to develop values of the required parameters. Such developed values of the parameters may then be supplied as inputs to the selected model to determine if the cells disposed in the well 118 associated with such parameters are responsive to the treatment associated with the model.

Figure 5:
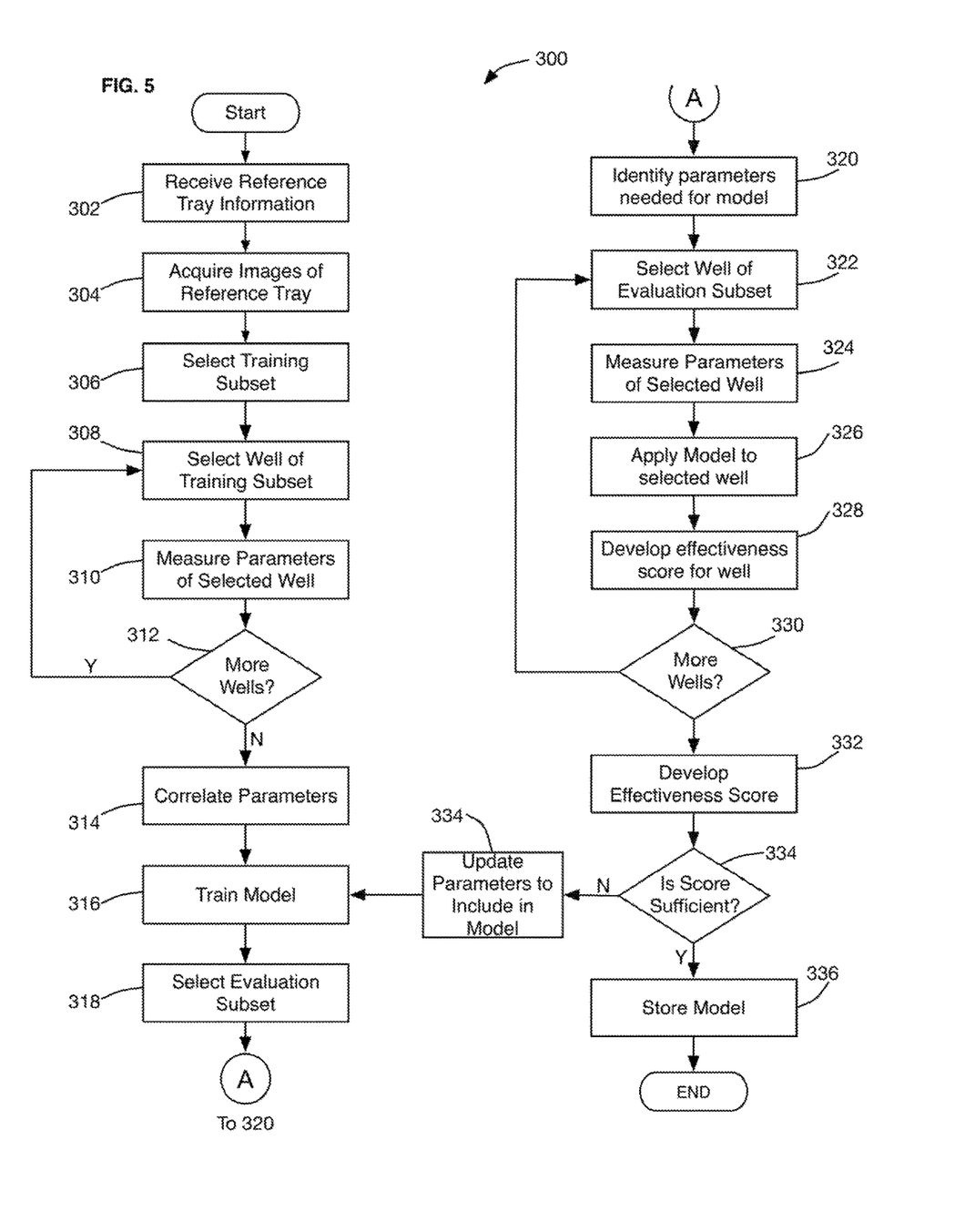
FIG. 5 is a flowchart of steps undertaken by the response analysis system of FIG. 2 to develop a model.

FIG. 5 shows a flowchart 300 of processing that may be undertaken by the response analysis system 200 to develop the trained model. At step 302, the user interface module 204 receives reference tray information from the user computer 202 and stores such information in the treatment information database 206. At step 304, the image acquisition module 208 captures images of each well 118A of the reference tray 116A, and stores such images in the images database 210.

After the images are stored, the model development module 212 selects a training subset of the wells 118A, at step 306. At step 308, the model development module 212 selects one of the wells 118A of the training subset that has not been analyzed, and provides the images associated with such well 118A in the images database 210 to the parameter calculation module 214. At step 310, the parameter calculation module 214 analyzes such images, and develops values of various parameters of such images and/or cells identified in such images.

At step 312, the model development module 212 determines if there is any well 118A of the training subset that has not been analyzed by the parameter calculation module 214. If so, processing proceeds to step 308.

Otherwise, at step 314, the model development module 212 correlates the concentration of treatment supplied to each well 118A of the training subset and the values of parameters development from images associated with such well. The model development module 212 uses those parameters that have the highest correlation to train a model, at step 316.

In one embodiment, all of the parameters that have a correlation greater than a predetermined value are used to train the model. If too many parameters are used, overfitting may occur in which parameters become correlated by happenstance and may not be have a high predictive value when used to evaluate other samples. Increasing the number of samples used to develop the correlations between the characteristics of the parameters and the treatments applied to the wells 118A may reduce such overfitting.

At step 318, the model evaluation module 218 selects a subset of the wells 118A of the reference sample tray 116A as an evaluation subset. At step 320, the model evaluation module 218 determines which parameters of each image are required to apply the model developed at step 316. In one embodiment, each parameter may be evaluated to determine how well such parameter by itself (i.e., without other parameters) is correlated with the amount of treatment applied to each well 118A of the reference sample tray 116A. Individual parameters that exhibit a high correlation without other parameters may be used to train the model. After the model is trained, additional parameters may be added or modified to improve the accuracy of the model. In other embodiments, a predetermined set of parameters may be used initially to train the model, and then additional parameters may be added to tune the model.

At step 322, the model evaluation module 218 selects one of the wells 118A of the evaluation subset that has not been analyzed, and provides the images from the images database 210 associated with the selected well and the parameters identified at step 320 to the parameter calculation module 214. At step 324, the parameter calculation module 214 analyzes such images and calculates the values of the identified parameters, and supplies the calculated values to the model evaluation module 218.

At step 326, the model evaluation module 218 uses the values of the parameters calculated from the images of the selected well 118A as inputs to the model to develop a prediction of whether any cells in the selected well 118A of the evaluation subset has a phenotypical response to the treatment, and, if so, the concentration of such treatment. Thereafter, the model evaluation module 218, at step 328, compares the predicted response from the model with the treatment information associated with the selected well 118A in the treatment information database 206, and develops an effectiveness score for the selected well 118A. The effectiveness score for the selected well 118A may be developed in a manner similar to that described above to develop the confidence score.

At step 330, the model evaluation module 218 determines if any wells 118A of the evaluation subset remain to be analyzed, and if so, proceeds to step 322. Otherwise, at step 332, the model evaluation module 218 aggregates the effectiveness scores for all of the wells 118A of the evaluation subset to develop an effectiveness score for the model.

At step 334, the model evaluation module 218 determines if the effectiveness score for the model is sufficient, for example, by comparing such score with a predetermined threshold or asking the operator. If the model effectiveness score is sufficient, then the model evaluation module 218 stores the model in the model database 216. When storing the model the operator may be asked, via the user interface module 204 to enter information that may be used to identify the model. Such information may include, for example, a name for the model, cell type and treatment type associated with the model, the operator who created the model, and the like. Such operator supplied information and automatically generated information, such as date when the model was created and the parameters that are necessary to run the model, are stored with the model in the model database 216.

If the model effectiveness score is not sufficient, then, at step 334, the model development module 212 modifies the parameters associated with inputs of the model and proceeds to step 316 to train the adjusted model. In some embodiments, there may be limits as to the number training iterations that may be used to train the adjusted model before a determination is made that the model is not converging. Such determination may be presented to the user and the user may request that further iterations be used or that training be stopped.

The model stored in the model database 216 may be retrieved thereafter to automatically process a production sample tray 116.

Figure 6:
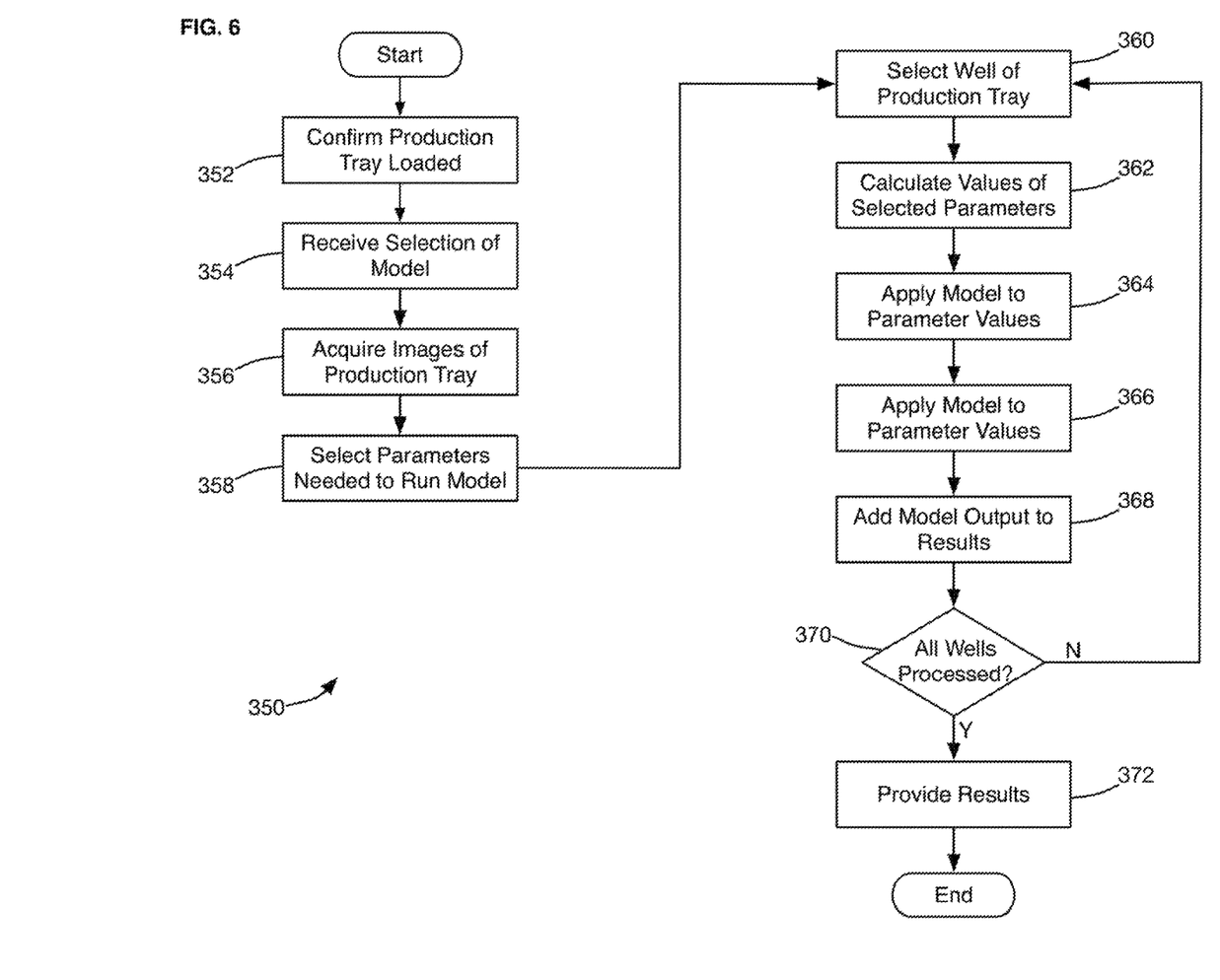
FIG. 6 is a flowchart of steps undertaken by the response analysis system of FIG. 2 to apply the model developed in accordance with the flowchart of FIG. 5.

FIG. 6 shows a flowchart 350 of the processing undertaken by the response analysis system 200 to process the production sample tray 116. At step 352, the model application module 220 communicates with the controller 112 of the HCIS 100 to confirm that the production sample tray 116 is loaded on the X-Y stage 102.

At step 354, the model application module 220 retrieves a list of models stored in the model database 216. The list of models and identifying information associated with each model are provided to the user interface module 204 for display on the user computer 202. Thereafter, the operator is asked to select the model. The user interface module 204 receives such selection and provides the selection to the model application module 220, also at step 354.

At step 356, the image acquisition module 208 directs the HCIS 100 to capture images of the wells 118 of the production sample tray 116, and stores such images in the images database 210.

At step 358, the model application module 220 queries the model database 216 to identify the parameters that are necessary to run the model. At step 360, the model application module 220 selects a well 118 of the production tray and provides the identified parameters and the images associated with such well 118 to the parameter calculation module 214.

At step 362, the parameter calculation module 214 calculates values of each of the parameters identified at step 358. At step 364 the model evaluation module 218 uses such calculated values as inputs to the model, and determines an output that indicates whether the cells disposed in the well 118 selected at step 360 exhibit a phenotypical response to the treatment, and, if so, the concentration of the treatment associated with such response.

Such output is added to a list of results, at step 368, that includes an entry for each well 118 of the production sample tray 116, and each entry includes the output of applying the model to the images associated with such well 118.

At step 370, the model application module 220 determines if all of the wells 118 of the production sample tray 116 have been processed using the model. If any wells 118 remain, the model application module 220 proceeds to step 360. Otherwise, at step 372, the model application module 220 provides the results to user interface module 204 for display on the user computer 202, stores such results in a data store (not shown) that may be accessed by the operator, and/or transmits such results to another system (not shown) for further analysis.

The response analysis system 200 may be used to determine how cells respond to different doses of treatment, to evaluate the effect a pharmaceutical product has on cells, or the types of cells that may be affected by a pharmaceutical product. The response analysis system 200 may help a researcher identify the types of cells that respond to the treatment or to identify commonality in cells that are responsive to a particular treatment. In addition, the response analysis system 200 may allow the operator to identify which treatment or dose of a treatment is effective in killing certain types of cells (e.g., cancer cells) but not other types of cells. Further, the response analysis system 200 may be used to identify particularly hearty cells that may be appropriate for cloning. The response analysis system 200 may also be evaluate the phenotypical response of organelles within cells in an image.

As noted above, the response analysis system 200 may be used to evaluate or identify the phenotypical response of a particular type of cell in a hetrogenous population of cells disposed in the well 118 of a sample tray. For example, the phenotypcal response to a treatment of neurons may be evaluated in a population that includes neurons and glial cells, or even the phenotypical response of live cells in a population that includes live cells and dead cells.

Different models developed as described above may be used in combination to identify different phenotypical responses to treatments applied to wells 118 of a sample tray 116. For example, a first model associated with a treatment of cells may be applied to images of wells 118 of a particular sample tray 116 to evaluate the phenotypical response of the cells in such wells 118 to the treatment. A second model associated with a different treatment then may be applied to the images of the wells 118 of the same sample tray 116 to evaluate the phenotypical response of the cells in the wells 118 to the second treatment. The first model and the second model may be used to evaluate the phenotypical response of identical types of cells or different types of cells. In some embodiments, the first model may be used to evaluate the phenotypical response of live cells and the second model may be used to evaluate the number of deceased cells in the wells 118 of the sample tray 116.

As noted above, different models developed may be used in combination (i.e., multiplexed) to identify multiple responses of individual cells or to identify responses of individual cells. In some embodiments, the combined models may be used to identify the percent of healthy cells that are responsive to the treatment, the number of cells undergoing cell division that are producing a certain protein, the number of infected cells (e.g., infected with bacteria or virus) that are absorbing a particular molecule, and the like.

In some embodiments, the response analysis system 200 may be used to develop a model that is trained with images of wells 118 treated with a drug that has a known effect on cells but also has an undesirable characteristic as a pharmaceutical agent. The model may be used to evaluate the effects on cells of other drug candidates. In another application, the response analysis system 200 may be used to determine how cells respond to known agents after being modified through treatment.

Although the response analysis system 200 above is described in the context of identifying cells in an image, it should be apparent that such system may be used identify the response of any type of object of which an image may be acquired.

Although the response analysis system 200 has been described above with respect to samples of cells deposited in wells 118 of a tray 116, it should be apparent that the response analysis system 200 may be used to automatically analyze the phenotypical response of cells provided in other types of carriers. For example, instead of a well 118 of a tray 116 in which a particular amount of treatment has been applied to each well 118, the cells may be provided on a set of slides in which a particular amount of treatment has been applied to each slide. Similarly, the cells may be provided in discrete samples of fluids in a flow cytometry system, and each such sample of fluid may be analyzed as the well 118 is analyzed in the description above above.

It will be understood and appreciated that one or more of the modules, processes, sub-processes, and process steps described in connection with FIGS. 1-6 may be performed by hardware, software, or a combination of hardware and software on one or more electronic or digitally-controlled devices. The software may reside in a software memory (not shown) in a suitable electronic processing component or system such as, for example, one or more of the functional systems, controllers, devices, components, modules, or sub-modules schematically depicted in FIGS. 1-6. The software memory may include an ordered listing of executable instructions for implementing logical functions (that is, "logic" that may be implemented in digital form such as digital circuitry or source code, or in analog form such as analog source such as an analog electrical, sound, or video signal). The instructions may be executed within a processing module or controller (e.g., the user interface module 204, the image acquisition module 208, the model development module 212, the parameter calculation module 214, the model evaluation module 218, and the model application module 220), which includes, for example, one or more microprocessors, general purpose processors, combinations of processors, digital signal processors (DSPs), field programmable gate arrays (FPGAs), or application-specific integrated circuits (ASICs). Further, the schematic diagrams describe a logical division of functions having physical (hardware and/or software) implementations that are not limited by architecture or the physical layout of the functions. The example systems described in this application may be implemented in a variety of configurations and operate as hardware/software components in a single hardware/software unit, or in separate hardware/software units.

The executable instructions may be implemented as a computer program product having instructions stored therein which, when executed by a processing module of an electronic system, direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this document, computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access, i.e., volatile, memory (electronic); a read-only memory (electronic); an erasable programmable read only memory such as, for example, Flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that receiving and transmitting of data as used in this document means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

INDUSTRIAL APPLICABILITY

The use of the terms "a" and "an" and "the" and similar references in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Numerous modifications to the present disclosure will be apparent to those skilled in the art in view of the foregoing description. It should be understood that the illustrated embodiments are exemplary only, and should not be taken as limiting the scope of the disclosure.

We claim:

1. A system to analyze a phenotypical response of cells to a treatment, comprising:
   a high-content imaging system, wherein the high-content imaging system includes an image capture device; and
   a response analysis system that includes computer-executable code stored on one or more non-transitory storage devices that, when executed, causes one or more processors to:
   receive images of a plurality of reference cell carriers and treatment information associated with the plurality of reference cell carriers, identify parameters of cells in the plurality of reference cell carriers from the images based on the treatment information, the parameters distinguishing those cells in the plurality of reference cell carriers to which the treatment has been applied from other cells in the plurality of reference cell carriers, and train a model using the identified parameters,
   receive from the image capture device a plurality of images of cell carriers to be evaluated, and
   apply the trained model to the plurality of images of the cell carriers to be evaluated to indicate a response level of cells in each of the cell carriers to be evaluated.

2. The system of claim 1, wherein the images of the plurality of reference cell carriers are one of images of wells of a reference tray, images of a set of slides, and images of flow cytometry fluid samples.

3. The system of claim 1, wherein the high-content imaging system includes a controller that automatically operates the image capture device to capture images of each of the cell carriers to be evaluated using a plurality of combinations of an objective lens, one or more filters, and illumination.

4. The system of claim 1, wherein the computer-executable code further causes the one or more processors to select a first subset of the plurality of reference cell carriers as a training subset and a second subset of the plurality of reference cell carriers as an evaluation subset, use images of the training subset to train the model and images of the evaluation subset to evaluate effectiveness of the model, and select parameters of the images of the training subset to use to train the model.

5. The system of claim 4, wherein the computer-executable code further causes the one or more processors to evaluate characteristics of parameters associated with each of the plurality of images of the training subset, and analyze each of the plurality of images of the training subset to identify locations of cell nuclei in each such image.

6. The system of claim 4, wherein the model is a deep learning neural network in which images are provided to input nodes thereof.

7. The system of claim 4, wherein the model is an artificial neural network in which each input node is associated with a selected parameter.

8. The system of claim 5, wherein the model is trained using one of deep learning, forest try, random forest, genetic algorithm, metaheuristic, k-means clustering, ant swarming, ant colony optimization, and simulated annealing techniques.

9. The system of claim 1, wherein the computer-executable code further causes the one or more processors to calculate an effectiveness of the model developed by the model development module.

10. The system of claim 1, wherein the model is used in combination with additional models to identify cells that exhibit a plurality of types of responses.

11. A method for analyzing a phenotypical response of cells to a treatment, comprising:
    operating a high-content imaging system, wherein the high-content imaging system includes an image capture device;
    receiving images of a plurality of reference cell carriers and treatment information associated with the plurality of reference cell carriers;
    identifying parameters of cells in the plurality of reference cell carriers from the images, the parameters distinguishing those cells in the plurality of reference cell carriers to which the treatment has been applied from other cells in the plurality of reference cell carriers;
    training a model using the identified parameters;
    operating the image capture device of the high-content imaging system to obtain a plurality of images of cell carriers to be evaluated; and
    applying the trained model to the plurality of images of the cell carriers to be evaluated to predict a concentration of the treatment applied to each cell carrier of the plurality of cell carriers to be evaluated.

12. The method of claim 11, wherein the images of the plurality of reference cell carriers are one of images of wells of a reference tray, images of a set of slides, and images of flow cytometry fluid samples.

13. The method of claim 11, including the further step of automatically selecting an objective lens, one or more filters, and illumination used by the high-content imaging system to capture images of each of the cell carriers to be evaluated.

14. The method of claim 11, including the further step of selecting a first subset of the plurality of reference cell carriers as a training subset and a second subset of the plurality of reference cell carriers as an evaluation subset, wherein training the model includes using images of the training subset to train the model and images of the evaluation subset to evaluate effectiveness of the model.

15. The method of claim 14, including the further step of selecting parameters of the images of the training subset to use to train the model.

16. The method of claim 15, further including the step of evaluating characteristics of parameters associated with each of the plurality of images of the training subset.

17. The method of claim 16, further including the step of analyzing each of the plurality of images of the training subset to identify locations of cell nuclei in each such image.

18. The method of claim 15, wherein the model is an artificial neural network in which each input node is associated with a selected parameter.

19. The method of claim 15, further including the step of training the model with one of deep learning, forest try, random forest, genetic algorithm, metaheuristic, k-means clustering, ant swarming, ant colony optimization, and simulated annealing techniques.

20. The method of claim 11, further including the step of calculating an effectiveness of the developed model.

\* \* \* \* \*